United States Patent [19]

Prencipe et al.

[11] Patent Number: 5,256,402
[45] Date of Patent: Oct. 26, 1993

[54] ABRASIVE TOOTH WHITENING DENTIFRICE OF IMPROVED STABILITY

[75] Inventors: Michael Prencipe, East Windsor, N.J.; Vincent Drago, Staten Island, N.Y.

[73] Assignee: Colgate-Palmolive Company, Piscataway, N.J.

[21] Appl. No.: 759,244

[22] Filed: Sep. 13, 1991

[51] Int. Cl.⁵ .................... A61K 7/20; A61K 33/40
[52] U.S. Cl. ...................... 424/53; 424/613; 424/616
[58] Field of Search .................. 424/53, 613, 616

[56] References Cited

U.S. PATENT DOCUMENTS

| | | |
|---|---|---|
| 3,577,521 | 5/1971 | Scholler et al. ............ 424/57 |
| 4,022,881 | 5/1977 | Hawkins ..................... 424/49 |
| 4,041,149 | 8/1977 | Gaffar et al. ............... 424/601 |
| 4,062,793 | 12/1977 | Schodel ..................... 424/53 |
| 4,181,621 | 1/1980 | Raaf ......................... 424/53 |
| 4,223,003 | 9/1980 | Scheller .................... 424/53 |
| 4,350,681 | 9/1982 | Fulton ....................... 424/53 |
| 4,405,599 | 9/1983 | Smigel ....................... 424/53 |
| 4,522,805 | 6/1985 | Gordon ...................... 424/53 |
| 4,592,487 | 6/1986 | Simon et al. ............... 424/53 |
| 4,603,045 | 7/1986 | Smigel ....................... 424/53 |
| 4,647,451 | 3/1987 | Piechota ..................... 424/57 |
| 4,670,252 | 6/1987 | Sampathkumar .............. 424/53 |
| 4,812,308 | 3/1989 | Winston et al. ............. 424/53 |
| 4,837,008 | 6/1989 | Rudy et al. ................. 424/53 |
| 4,867,988 | 9/1989 | Chernock .................... 424/53 |
| 4,891,211 | 1/1990 | Winston ..................... 424/53 |
| 4,895,721 | 1/1990 | Drucker ..................... 424/53 |
| 4,897,258 | 1/1990 | Rudy et al. ................. 424/53 |
| 4,971,782 | 11/1990 | Rudy et al. ................ 424/53 |
| 4,976,955 | 12/1990 | Libin ........................ 424/53 |
| 4,980,154 | 12/1990 | Gordon ...................... 424/53 |
| 4,988,500 | 1/1991 | Hunter et al. ............... 424/53 |
| 5,000,941 | 3/1991 | Chernack .................... 424/53 |
| 5,015,466 | 5/1991 | Parran et al. ............... 424/52 |
| 5,041,280 | 8/1991 | Smigel ....................... 424/53 |
| 5,084,268 | 1/1992 | Thaler ....................... 424/53 |
| 5,085,853 | 2/1992 | Williams et al. ............ 424/53 |
| 5,114,718 | 5/1992 | Damani ...................... 424/422 |
| 5,122,365 | 6/1992 | Murayama ................... 424/49 |
| 5,171,564 | 12/1992 | Nathod et al. .............. 424/53 |
| 5,186,926 | 2/1993 | Williams et al. ............ 424/53 |

*Primary Examiner*—Shep K. Rose
*Attorney, Agent, or Firm*—Paul Shapiro; Robert C. Sullivan

[57] ABSTRACT

Abrasive dentifrice compositions containing an oxygen liberating whitening compound which is stable with respect to oxygen level and exhibits heightened and rapid whitening of teeth and stain removal which comprises a combination of a dicalcium phosphate compound and a metal ion free peroxide compound.

12 Claims, No Drawings

ABRASIVE TOOTH WHITENING DENTIFRICE OF IMPROVED STABILITY

BACKGROUND OF THE INVENTION

1. Field of the Invention This invention relates generally to preparations for whitening human teeth, and more particularly, to a stable, storable composition which when applied onto the surface of teeth acts to whiten and polish teeth without damage to oral tissues.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a pellicle film over the teeth. These staining and discoloring substances can then permeate the enamel layer. This problem occurs gradually over many years, but imparts a noticeable discoloration of the enamel of one's teeth.

Dentifrices, especially toothpaste, gels and powders containing active oxygen or hydrogen peroxide liberating ingredients such as peroxides, percarbonates and perborates of the alkali and alkaline earth metals or complex compounds containing hydrogen peroxide with salts of the alkali or alkaline earth metals have been disclosed in the prior art for the whitening of teeth. However, of all the peroxide compounds suggested by the prior art for whitening teeth, only two peroxide releasing compounds, urea peroxide and hydrogen peroxide, are approved by the Food and Drug Administration for use in oral compositions.

One method for whitening teeth used by dental professionals involves the use of 35% hydrogen peroxide in combination with heat and light to promote the oxidation reaction. This method, although fast, is losing favor with dentists because clinical and scientific evidence shows that high concentrations of peroxide are deleterious to oral tissues.

Another professional method for whitening teeth involves the use of hydrogen peroxide generating compounds such as urea peroxide (carbamide peroxide) at concentrations of about 10% to achieve the desired whitening effect. Urea peroxide rapidly breaks down into hydrogen peroxide due to the water present in saliva. This method is known as an office-monitored at-home bleaching system and involves the use of a mouth guard or tray within which the bleaching agent is placed. The tray is then placed upon the teeth of the patient and bleaching is allowed to take place. This method of treatment has drawbacks including tooth sensitivity, possibly due to demineralization and irritation of oral tissues. An additional disadvantage of the tray application method is that the bleaching effect is very slow.

There is a demand in the marketplace for a tooth whitening product that can be used at home or in private by the consumer and is safe and easy to use. A product for home use cannot utilize the compositions or products for whitening teeth that are available for use by a trained dental professional. For example, the 35% hydrogen peroxide bleaching agent utilized by many dental practitioners to bleach teeth is sufficiently concentrated to be irritating and potentially dangerous for home use by the consumer.

There are available in the marketplace non-abrasive dentifrice compositions for home use which contain 1–3% by weight concentrations of hydrogen peroxide and when brushed on the teeth effect whitening and removal of stains.

A drawback to the use of home use bleaching dentifrices containing oxygen liberating bleaching compounds is the tendency of these products to decompose within a relatively short period of time following manufacture with concomitant loss of all or a substantial amount of the available oxygen thereby limiting the efficacy of these products as teeth whitening compositions. Peroxy compounds such as hydrogen peroxide are notoriously unstable with respect to maintenance of peroxide level and have been found to be difficult to formulate into aqueous gels or pastes which will have an adequate shelf-life and yet will readily liberate oxygen when applied to the oral cavity. Therefore, the prior art, for example U.S. Pat. No. 4,988,450 and U.S. Pat. No. 3,657,413 in formulating oxygen liberating compositions for the whitening of teeth utilize anhydrous powders or water-free pastes or gels which must be protected against contamination and chemical interaction. A drawback to the use of such anhydrous products is that, due to the absence of water, application of the oral composition tends to desiccate oral tissues which leads to irritation and tissue damage.

Dentifrice whitening products formulated with peroxy compounds normally do not contain abrasive polishing agents as such materials activate the rapid decomposition of the peroxy compounds whereby the oxygen whitening agent is prematurely released. The gas evolution is especially undesirable with a toothpaste or gel product as such gas evolution can cause swelling and/or bursting of tubes containing same. Capped tubes filled with dentifrice products containing peroxy compounds and silica abrasives have been known to explode within one day after filling. When alumina abrasives are substituted for silica, the filled product is pocketed with gas bubbles within days of filling.

A drawback to the use of whitening products which are formulated without abrasives is that, in addition to having a slow bleaching action, the products are not effective in stain removal. Thus the polishing agent incorporated in a dentifrice acts to debride and physically scrub the external surface of teeth. This scrubbing action removes filmy bacterial and plaque layers as well as some of the stains and discoloring pigments that are found on teeth that cause the undesired discoloration. These polishing agents also microabrade the tooth so as to polish the teeth to give the enamel a more lustrous appearance and a higher optical sheen. This microabrasion action enhances the scrubbed teeth's ability to reflect white light and thereby appear brighter.

Illustrative of non-abrasive oral compositions containing peroxide compounds include U.S. Pat. Nos. 4,980,152; 4,839,156; 4,522,805 and 4,567,036.

U.S. Pat. No. 4,980,152 discloses a non-abrasive aqueous oral gel composition comprising about 0.5 to about 10% by weight urea peroxide and 0.01 to 2% by weight of a fluoride providing compound. The composition further includes a thickening agent such as carboxy polymethylene, a non-ionic surfactant such as Pluronic F127, alkali soluble cellulose ethers as viscosity increasing agents, potassium phosphate as a buffering agent and glycerine as a carrier and flavoring and sweetening agents.

U.S. Pat. No. 4,839,156 discloses an aqueous dental gel containing 18-25% by weight of a polyoxyethylene polypropylene block copolymer gelling agent, hydrogen peroxide, flavor, sweetening agent and a non-ionic surfactant as the essential ingredients.

U.S. Pat. Nos. 4,522,805 and 4,567,036 disclose a stable toothpaste to aid in controlling periodontal disease, containing an oxidizing agent such as carbamide peroxide (urea peroxide) which dissociates into urea and hydrogen peroxide in the oral cavity, in a paste carrier comprising an anionic detergent, sorbitol and glycerin humectant and a thickening agent such as gum tragacanth, sodium alginate or sodium carboxymethyl cellulose.

U.S. Pat. No. 4,405,599 discloses a toothpaste consisting essentially of a combination of calcium peroxide and sodium perborate oxidizing agents, dicalcium phosphate dihydrate, calcium carbonate and magnesium carbonate cleaning agents, sorbitol humectant, cornstarch and cellulose gum thickening agents, and an anionic detergent.

SUMMARY OF THE INVENTION

In accordance with the present invention, it has now been found that abrasive dentifrice compositions which contain a peroxide compound which is stable with respect to active oxygen level and exhibits heightened and rapid whitening of teeth and stain removal is obtained when using a combination of a dicalcium phosphate compound and a metal ion free peroxide compound.

As will hereinafter be illustrated, the dentifrice compositions of the present invention exhibit better peroxide efficacy in removing stains from teeth than previously attained by the prior art. The compositions are stable at elevated temperatures, and can be used for both office monitored at-home applications as well as private brushing applications.

DESCRIPTION OF THE PREFERRED EMBODIMENTS

The term "dicalcium phosphate compound" as used herein includes within its meaning both dicalcium phosphate-dihydrate and anhydrous dicalcium phosphate or calcium pyrophosphate. Dicalcium phosphate-dihydrate and calcium pyrophosphate are compounds which have long been used as cleaning agents in toothpastes. These calcium phosphate compounds have remineralizing properties, their ionic constituents are practically the same as those contained in dental enamel, which they combine with the property of imparting excellent cleaning and polishing effects to oral compositions made therefrom. A high beta phase calcium pyrophosphate is preferred as the dicalcium phosphate compound for use in the present invention.

The dentifrice compositions of the present invention are formulated using a metal ion free peroxide compound as the whitening agent, a dicalcium phosphate compound as the abrasive polishing agent, a humectant, a surfactant, a sweetener and flavor.

Examples of suitable metal ion free peroxide compounds used to prepare the oral compositions of the present invention include hydrogen peroxide and organic peroxides including urea peroxide (percarbamide), glyceryl peroxide, benzoyl peroxide and the like. A preferred organic peroxide is urea peroxide.

The peroxide component of the composition of the invention is included in an amount sufficient to allow release of sufficient oxygen when the composition is contacted with water, e.g., during brushing of teeth, to effect whitening thereof. Typically, the peroxide can be employed in the composition of the present invention in amounts so that at least about 1% of the composition comprises a peroxide. Preferably, the peroxide comprises from about 1 to about 20% by weight of the composition. More preferably, the peroxide comprises from about 5 to about 15% by weight of the composition. The active peroxide content (i.e., the equivalent of $H_2O_2$ in the peroxide employed) is preferably between about 0.5 and about 6% by weight, and more preferably between about 1 and about 3% by weight.

The presence of a dicalcium phosphate compound in the composition of the present invention in addition to its polishing function has been found to provide significant increased peroxide stability of the compositions in comparison to compositions with other abrasives. For example, when 40% by weight of calcium pyrophosphate was employed in combination with 10% by weight urea peroxide in a polyethylene glycol carrier, a 95% residual peroxide level was found after storage of the composition in a closed container for 14 days at elevated temperatures (e.g. 100° F.).

In preparing the dentifrice compositions of the present invention, the dicalcium phosphate compound is included in the composition of the invention in an amount effective so as to inhibit breakdown of the peroxide in the composition during storage in a closed container, but so as to allow release of sufficient oxygen from the peroxide when the composition is contacted with water, e.g., during brushing of teeth, to effect whitening thereof. Typically, the dicalcium phosphate compound is included in the composition of the present invention in an amount of from 20 to about 60% by weight, preferably from about 35 to about 55%.

Polyethylene glycols are preferred as the carrier. Illustrative of the polyethylene glycols useful in the practice of the present invention include polyethylene glycols known by the trademark CARBOWAX which are nonionic polymers of ethylene oxide having the general formula:

wherein n represents the average number of oxyethylene groups. The Carbowax polyethylene glycols are designated by a number such as 400, 600, 800, etc. which represents the average molecular weight. The molecular weight range of the polyethylene glycols used herein is about 200 to about 20,000 and preferably from about 600 to about 8,000. Such materials range from thin liquids to pastes, to solids with increasing molecular weight.

A surfactant is also included in the dentifrice composition of the present invention and serves as a solubilizing, dispersing, emulsifying and wetting agent and is especially effective in solubilizing the flavor present. A particularly useful surfactant is a nonionic water soluble polyoxyethylene monoester of sorbitol with a $C_{10-18}$ fatty acid ester of sorbitol (and sorbitol anhydrides), consisting predominantly of the monoester, condensed with about 10-30, preferably about 20, moles of ethyleneoxide. The fatty acid (aliphatic hydrocarbon-monocarboxylic acid) may be saturated or unsaturated, e.g. lauric, palmitic, stearic, oleic acids. Tween 20 is especially preferred, which is a polyoxyethylene (20) sorbitan monolaurate. The nonionic surfactant constitutes about 0.5 to 5.0% by weight and preferably 0.5 to 3% by weight of the oral composition.

Other classes of surfactants such as cationic surfactants, anionic surfactants such as sodium laurylsulfate and sodium laurylsulfoacetate, ampholytic and amphoteric surfactants like cocoamidopropyl betaine can also be employed.

The flavor ingredient constitutes about 0.5-5.0% by weight of the dentifrice composition of the present invention. Suitable flavoring constituents are flavoring oils, e.g., oils of spearmint, peppermint, wintergreen, sassafras, clove, sage, eucalyptus, marjoram, cinnamon, ethyl acetate, methyl salicylate, and menthol.

A sweetening material is preferably also employed as a complement to the flavoring material. Suitable sweetening agents are water soluble and include sodium saccharin, sodium cyclamate, xylitol, aspartame and the like, in concentrations of about 0.01 to 1.0% by weight. Sodium saccharin is preferred.

Thickening or gelling agents may also be used in the formulation of the dentifrice. Thickening agents include natural and synthetic gums and gum-like materials, such as carrageenan, Xanthan gum, alkali metal (e.g., K, Na) carboxymethyl cellulose and hydroxymethyl carboxymethyl cellulose, polyvinyl pyrolidone, water soluble hydrophilic colloidal carboxyvinyl polymers such as those sold under the trademark Carbopol 934 and 940, hydroxyethyl cellulose, India gum, locust bean gum, agar, modified starches, inorganic thickeners such as colloidal silica, e.g. synthetic finely-divided silica including those sold under the trademarks Cab-O-Sil Syloid, and Aerosil, or crosslinked polycarboxylate polymers available from GAF under the designation Gantrez ACV series. The thickening and gelling agents are preferably present in the dentifrice in an amount within the range of about 0.3 to about 6% by weight.

Other useful thickening agents included in the composition of the present invention are polyoxyethylene polyoxypropylene block copolymers in amounts from about 10% to about 25% by weight of the composition. Illustrative of the polyoxyethylene polyoxypropylene block copolymers useful in the practice of the present invention include block copolymers having the formula $HO(C_2H_4O)_b(C_3H_6O)_a(C_2H_2O)_bH$ wherein a is an integer such that the hydrophobic base represented by $(C_3H_6O)$ has a molecular weight of about 2750 to 4000, b is an integer such that the hydrophilic portion (moiety)represented by $(C_2H_4O)$ constitutes about 70-80% by weight of the copolymer. Block copolymers of this composition are available commercially under the trademark Pluronic F type.

Pluronic F127, which has a molecular weight of 4000 and contains 70% of the hydrophilic polyoxyethylene moeity is preferred in the practice of the present invention.

Fluorine-providing salts having anti-caries efficacy may also be incorporated in the dentifrice of the present invention and are characterized by their ability to release fluoride ions in water. Among these materials are inorganic metal salts, for example, sodium fluoride, potassium fluoride, cuprous fluoride, a tin fluoride such as stannous fluoride or stannous chlorofluoride, sodium fluorosilicate, ammonium fluorosilicate, sodium monofluorophosphate, alumina mono-and di-fluorophosphate.

It is preferable to employ a fluoride compound to release about 10-1,500 ppm of fluoride ion.

Pyrophosphate salts having anti-tartar efficacy such as a dialkali or tetra-alkali metal pyrophosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphates such as sodium trimeta phosphate are incorporated in the dentifrice products of the present invention preferably at a concentration of about 0.5 to about 8.0% by weight.

Synthetic anionic linear polymeric polycarboxylates which are employed in the form of their partially or preferably fully neutralized water soluble alkali metal (e.g. potassium and preferably sodium) or ammonium salts may also be incorporated in the dentifrice compositions of the present invention. Preferred are 1:4 to 4:1 copolymers of maleic anhydride or acid and a polymerizable ethylenically unsaturated monomer, preferably a lower alkyl vinyl ether such as methoxyethylene, having a molecular weight of about 30,000 to about 1,000,000 available commercially from GAF Corporation under the trademark Gantrez. A preferred polycarboxylate for use in the present invention is Gantrez S-97 which has a molecular weight of 97,000. The polycarboxylate compounds are incorporated in the compositions of the present invention at a concentration of about 0.1 to about 5% by weight and preferably about 0.3 to about 1.0 percent by weight.

The dentifrice product of this invention may also contain conventional additional ingredients such as coloring or whitening agents, or preservatives such as sodium benzoate, in minimal amounts of up to 5% by weight and preferably up to 1%, provided they do not interfere with the chemical and cosmetic (physical) stability properties of the finished product.

Peroxide stabilizers may also be added to the composition, such as sequestering agents, buffers, acidulating agents, coating or encapsulating agents. Examples of suitable sequestering agents are salts of ethylene diamine tetraacetic acid, diethylene triamine pentaacetic acid, phosphonates such as Dequest (trademark) available from Monsanto Chemical Company and azacycloheptane 2',2' diphosphonate. Such chelating agents stabilize the peroxide containing compositions by chelating metal ions such as $Fe^{+3}$, $Mn^{+2}$ and $Cu^{+2}$. The chelating agents may be incorporated in the compositions of the present invention at a concentration of about 0.1 to about 6.0% by weight of the composition.

Acidulating agents can be any organic acids like acetic acid, citric acid, lactic acid or gluconic acid. The acedulating agents are incorporated in the compositions of the present invention at concentrations of about 0.1 to about 6.0% by weight of the composition.

Examples of suitable coating agents for encapsulating the peroxide include Carbowax, gelatin, and mineral oil.

Agents used to diminish teeth sensitivity such as strontium chloride, potassium nitrate and potassium citrate can also be included in the compositions of the present invention at concentrations of about 0.1 to about 10% by weight.

In preparing the dentifrice compositions of the present invention, it is advantageous to maintain the pH of the composition in a near neutral or slightly acidic range, e.g., about 5.0 to about 7.5.

The dentifrice composition of the present invention may be prepared by suitably mixing the ingredients. For instance, a gelling agent such as carboxymethyl cellulose is dispersed with a humectant, water, polycarboxylate, peroxide compound, salts such as tetrasodium pyrophosphate, sodium acid pyrophosphate, sodium fluoride or sodium monofluoro- phosphate, and saccharin are then added and mixed. The dicalcium phosphate, surfactant, and flavor are then added. The ingredients are then mixed under vacuum for about 15-30 minutes. The resulting gel or paste is then tubed.

The following examples are further illustrative of the present invention, but it is understood that the invention is not limited thereto. All amounts and proportions referred to herein and in the appended claims are by weight unless otherwise indicated.

A series of toothpastes were prepared using the following ingredients:

| Ingredients | COMPOSITION NO. | | | | |
|---|---|---|---|---|---|
| | 1% | 2% | 3% | 4% | C % |
| Urea Peroxide | 10 | 10 | 10 | — | — |
| $H_2O_2$ | — | — | — | 3.0 | 3.0 |
| Calcium Pyrophosphate | 40 | 40 | 40 | 40 | — |
| Glycerine | q.s. to 100 | q.s. to 100 | — | — | — |
| PEG-600 | 5 | 5 | q.s. to 100 | q.s. to 100 | 15 |
| PEG-8000 | — | — | 8 | — | — |
| CMC | 1.3 | 1.3 | — | — | — |
| Cab-o-sil | — | — | — | 4 | — |
| Gantrez S-97 (solids) | 1.73 | 1.73 | — | — | — |
| $Na_4P_2O_7$ | 2 | 2 | — | 0.3 | — |
| $Na_2H_2P_2O_7$ | — | — | — | 1.7 | — |
| NaF | — | 25 ppm | — | — | — |
| Flavor | 1.5 | 1.5 | 1.5 | 1.5 | 1.5 |
| Tween 20 | 1.2 | 1.2 | 1.2 | 1.2 | 1.2 |
| DI $H_2O$ | 9.8 | 9.8 | — | 7.0 | q.s. to 100 |
| Pluronic F-127 | — | — | — | — | 20.0 |
| Saccharin | — | — | — | — | 0.2 |

Composition 1 was prepared by mixing glycerine, PEG 600 (polyethylene glycol 600) together with CMC (carboxymethyl cellulose), then adding Gantrez S-97, urea peroxide, $Na_2H_2P_2O_7$, and $Na_4H_2P_2O_7$. The mixture was placed in a double planetary vacuum mixer. Calcium pyrophosphate, flavor and surfactant (Tween 20) were added to the mixture and the ingredients mixed under vacuum for about 15-20 minutes. A homogeneous paste was obtained.

Composition 2 was prepared in the same manner as Composition 1 except that 25 ppm NaF was included in the composition.

Composition 3 was prepared by heating PEG 600 to 130° F., adding PEG 8000 (polyethylene glycol 8000) and urea peroxide. The mixture is then transferred to a double planatery vacuum mixer. Calcium pyrophosphate was added and the resulting paste mixed for 5 minutes. Flavor and surfactant were added and then mixed for an additional 15 minutes under vacuum.

Composition 4 was prepared by adding fumed silica (Cab-o-Sil) to PEG-600. Water, urea peroxide, $Na_4P_2O_7$ and $Na_2H_2P_2O_7$ were added and mixed until all the ingredients were well dispersed. To the resulting gel, calcium pyrophosphate, flavor oil and surfactant were added and mixed under vacuum for 15-20 minutes.

For comparative purposes, Composition C, a Pluronic gel formula containing 3% $H_2O_2$, was prepared following the procedure outlined in U.S. Pat. No. 4,839,156.

Compositions 1-4 were tested for whitening efficacy. Extracted human molars having a high degree of discoloration were exposed for 6 hours at 37° C. to Compositions 1-4 to determine the whiteness of the teeth.

Before the discolored teeth were exposed to Compositions 1-4, the color of the teeth was measured with a Gardner tristimulus colorimeter using values obtained from the CIE L*, a* and b* scale. This scale represents the mathematical approximation of the non-linear response of the eye to light.

A zero value for a* and b* means some shade of gray. Positive values for a* and b* indicate redness and yellowness. Negative a* and b* represents values for green and blue. After the 6 hour exposure time, the color of the teeth was again measured. The increase in whiteness is calculated using the equation delta $E = \sqrt{((delta\ L^*)^2 + ((delta\ a^*)^2 + (delta\ b^*)^2)}$ where delta E represents an increase in whiteness. Delta L*, delta a* and delta b* represent the changes that have occurred in these parameters after the bleaching process.

The delta E values are recorded in Table I. For purposes of comparison, the test procedure of Example I was repeated with the exception that comparative Composition C which did not contain calcium pyrophosphate was tested for whiteness. The results obtained with this comparative composition are also recorded in Table I below.

TABLE I

| Increase in Whiteness | |
|---|---|
| Composition | Delta E |
| 1 | 7.1 |
| 2 | 7.8 |
| 3 | 6.6 |
| 4 | 6.2 |
| C | 4.9 |

The data recorded in Table I show that when extracted human molars are exposed to compositions of the present invention which contain calcium pyrophosphate, they achieve an increase in whiteness which is on average 41% higher than teeth exposed to composition C, which does not contain calcium pyrophosphate abrasive.

EXAMPLE II

The chemical stability of compositions 1, 3 and 4 of Example I was determined by initially analyzing the compositions for active oxygen (AO) and then storing the composition for 2 week periods at elevated temperatures (100° F., 110° F.) and again analyzing the dentifrice for AO.

The results of these analyses are summarized in Table II below.

TABLE II

| Composition No. | pH | Composition Stability | | | AO % Recovery | |
|---|---|---|---|---|---|---|
| | | AO % Initial | AO % 2 wks @ 100° F. | 110° F. | 100° F. | 110° F. |
| 1 | 5.5 | 1.65 | 1.55 | — | 94 | — |
| 1 | 6.0 | 1.65 | 1.42* | — | 86 | — |
| 3 | 5.1 | 1.59 | 1.48 | 1.43 | 93 | 90 |
| 4 | 6.2 | 1.51 | 1.43 | 1.30 | 95 | 86 |

*Results are after 3 weeks.

The data recorded in Table II indicate that the stability of the peroxide dentifrices of the present invention is greater than 90% after 2 weeks at 100° F. and greater than 86% after 2 weeks at 110° F. indicating that these oral compositions are relatively stable.

For purposes of comparison, a commercially available dentifrice sold as a tooth whitening composition was purchased at a local store. Ingredients listed on the product label included: water, sorbitol, dicalcium phosphate dihydrate, sodium bicarbonate, aluminum hydroxide, magnesium carbonate, calcium carbonate, cellulose gum, calcium peroxide and sodium perborate. When the dentifrice was analyzed for active oxygen, and it was determined that there was none, indicating low storage stability of the peroxy compounds included in the dentifrice.

EXAMPLE III

The stain removal properties of Composition 4 of Example I is recorded in Table III below. An additional composition of the present invention was prepared designated Composition 5 which was prepared in the same manner as Composition 1 of Example I, except that the thickening agent was Gantrez cross-linked with 1, 9 decadiene, designated Gantrez ACV-4006. The cross-linked Gantrez was substituted for CMC in Composition 1. Composition 5 also did not contain $Na_4P_2O_7$ or $Na_2H_2P_2O_7$, or Gantrez S-97.

The stain removal properties of the compositions 4 and 5 are recorded in Table III below. The data recorded in Table III shows the stain removal efficacy of toothpastes obtained from bovine teeth stained with tea and coffee after 50 strokes of brushing with compositions 4 and 5.

TABLE III

| STAIN REMOVAL | |
|---|---|
| Composition No. | Delta E |
| 4 | 13.0 |
| 5 | 11.5 |
| C | 2.9 |

The data recorded in Table III demonstrate that the compositions of the present invention effect superior stain removal, especially when compared to Composition C, thereby demonstrating the improved efficacy in stain removal attainable with the combination of a dicalcium phosphate abrasive compound and a peroxide compound.

What is claimed is:

1. An aqueous abrasive toothpaste composition containing a peroxide compound which is stable with respect to active oxygen level and exhibits heightened and rapid whitening of teeth and stain removal which aqueous composition consists essentially of a mixture, stable and storable without a peroxide stabilizer, when filled into a closed container of at least 7% by weight water, and a combination of about 20 to about 60% by weight calcium pyrophosphate, at least about 1 to about 20% by weight of urea peroxide and about 0.5 to about 8.0% by weight of an alkali pyrophosphate salt, which combination is stable and effective to remove stain and whiten teeth in the oral cavity.

2. The composition of claim 1 wherein the composition also contains a humectant, surfactant and thickener.

3. The composition of claim 1 wherein the humectant is a polyethylene glycol having a molecular weight between about 200 to about 20,000.

4. The composition of claim 1 wherein the humectant is glycerine, sorbitol, xylitol, propylene glycol, or a mixture thereof.

5. The composition of claim 1 wherein the surfactant is a nonionic water soluble polyoxyethylene monoester of sorbitol with a $C_{10-18}$ fatty acid ester of sorbitol and sorbitol anhydrides.

6. The composition of claim 1 wherein the thickening agent is polyoxyethylene polyoxypropylene block copolymer.

7. The composition of claim 1 wherein the thickener is carboxymethyl cellulose.

8. The composition of claim 1 wherein the thickening agent is fumed colloidal silica.

9. The composition of claim 1 wherein an agent which diminishes teeth sensitivity selected from the group consisting of strontium chloride, potassium nitrate and potassium citrate is incorporated in the composition.

10. The composition of claim 1 wherein the pH of the composition is in the range of about 5.0 to about 7.5.

11. The composition of claim 1 wherein the alkali pyrophosphate salt is a dialkali or tetraalkali pyrophosphate salt.

12. The composition of claim 11 wherein the dialkali or tetraalkali pyrophosphate salt is $Na_4P_2O_7$ or $Na_2H_2P_2O_7$

* * * * *